United States Patent
Jang

(10) Patent No.: US 11,844,588 B2
(45) Date of Patent: Dec. 19, 2023

(54) APPARATUS AND METHOD FOR DETECTING CHARACTERISTIC POINT OF OSCILLOMETRIC ENVELOPE AND APPARATUS FOR ESTIMATING BIO-INFORMATION

(71) Applicant: SAMSUNG ELECTRONICS CO., LTD., Suwon-si (KR)

(72) Inventor: Dae Guen Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 623 days.

(21) Appl. No.: 16/880,498

(22) Filed: May 21, 2020

(65) Prior Publication Data

US 2021/0145288 A1    May 20, 2021

(30) Foreign Application Priority Data

Nov. 20, 2019    (KR) .................. 10-2019-0149334

(51) Int. Cl.
*A61B 5/00* (2006.01)
*A61B 5/02* (2006.01)
(Continued)

(52) U.S. Cl.
CPC .......... *A61B 5/0205* (2013.01); *A61B 5/0002* (2013.01); *A61B 5/022* (2013.01);
(Continued)

(58) Field of Classification Search
None
See application file for complete search history.

(56) References Cited

U.S. PATENT DOCUMENTS 6,808,496 B2    10/2004    Oka et al.
7,029,448 B2     4/2006    Kubo
(Continued)

FOREIGN PATENT DOCUMENTS

JP    2003-284696 A    10/2003
JP    2006-51197 A     2/2006
(Continued)

OTHER PUBLICATIONS

Chen et al. Assessment of Algorithms for Oscillometric Blood Pressure Measurement. International Instrumentation and Measurement Technology Conference, Singapore, May 5-7, 2009. (Year: 2009).*

(Continued)

*Primary Examiner* — Etsub D Berhanu
(74) *Attorney, Agent, or Firm* — Sughrue Mion, PLLC

(57) ABSTRACT

Provided is an apparatus for detecting a characteristic point to non-invasively estimate bio-information by analyzing a pulse waveform. The apparatus for detecting a characteristic point may include a bio-signal sensor that may obtain a bio-signal from an object, and a processor configured to obtain a first envelope by removing a first baseline change from an oscillometric waveform envelope of the bio-signal; obtain a second envelope by removing a second baseline change from the oscillometric waveform envelope of the bio-signal; obtain a third envelope based on the first envelope and the second envelope; and detect the characteristic point from the oscillometric waveform envelope based on the third envelope.

27 Claims, 14 Drawing Sheets

(51) Int. Cl.
    *A61B 5/0205* (2006.01)
    *A61B 5/022* (2006.01)
    *A61B 5/16* (2006.01)
    *A61B 5/021* (2006.01)
    *A61B 5/024* (2006.01)

(52) U.S. Cl.
    CPC .......... *A61B 5/02007* (2013.01); *A61B 5/165* (2013.01); *A61B 5/48* (2013.01); *A61B 5/72* (2013.01); *A61B 5/02116* (2013.01); *A61B 5/02125* (2013.01); *A61B 5/02225* (2013.01); *A61B 5/02416* (2013.01); *A61B 2560/0242* (2013.01); *A61B 2562/0247* (2013.01)

(56) References Cited

U.S. PATENT DOCUMENTS

| | | | |
|---|---|---|---|
| 8,652,055 | B2 | 2/2014 | Saitou |
| 2007/0118036 | A1* | 5/2007 | Hersh .................... A61B 5/022 600/490 |
| 2007/0270698 | A1 | 11/2007 | Saitou |
| 2008/0188760 | A1 | 8/2008 | Al-Ali et al. |
| 2015/0164339 | A1 | 6/2015 | Xu et al. |
| 2016/0058384 | A1 | 3/2016 | Chen |
| 2016/0081565 | A1 | 3/2016 | Kinoshita et al. |
| 2016/0081626 | A1 | 3/2016 | Takahashi |
| 2017/0118036 | A1 | 4/2017 | Yuh et al. |
| 2019/0313979 | A1 | 10/2019 | Kang et al. |

FOREIGN PATENT DOCUMENTS

| | | |
|---|---|---|
| JP | 2006-247216 A | 9/2006 |
| JP | 2015-9044 A | 1/2015 |
| JP | 2016-220886 A | 12/2016 |
| KR | 10-2012-0040429 A | 4/2012 |
| KR | 10-2019-0011592 A | 2/2019 |

OTHER PUBLICATIONS

Min Chen et al., "A Developed Algorithm for Oscillometric Blood Pressure Measurement", IEEE, 2013, 4 pages.

Soojeong Lee et al., "Oscillometric Blood Pressure Estimation Based on Maximum Amplitude Algorithm Employing Gaussian Mixture Regression", IEEE Transactions on Instrumentation and Measurement, vol. 62, No. 12, IEEE, Dec. 2013, pp. 3387-3389.

Pool Khoon Lim et al., "Improved Measurement of Blood Pressure by Extraction of Characteristic Features from the Cuff Oscillometric Waveform", Sensors, vol. 15, Jun. 16, 2015, pp. 14142-14161.

Qun Wang et al., "An Improved Algorithm for Noninvasive Blood Pressure Measurement", Bioelectronics and Bioinformatics (ISBB), 2011 International Symposium, 2011, pp. 41-44.

Communication dated Nov. 20, 2020 issued by the European Patent Office in counterpart European Patent Application No. 20182235.0.

\* cited by examiner

APPARATUS AND METHOD FOR DETECTING CHARACTERISTIC POINT OF OSCILLOMETRIC ENVELOPE AND APPARATUS FOR ESTIMATING BIO-INFORMATION

CROSS-REFERENCE TO RELATED APPLICATION(S)

This application claims priority from Korean Patent Application No. 10-2019-0149334, filed on Nov. 20, 2019, in the Korean Intellectual Property Office, the entire disclosure of which is incorporated herein by reference for all purposes.

BACKGROUND

1. Field

Example embodiments relate to technology for detecting characteristic points from an oscillometric envelope of a bio-signal, and estimating bio-information by using the detected characteristic points.

2. Description of Related Art

Recently, with the aging population, soaring medical costs, and a lack of medical personnel for specialized medical services, research has been actively conducted on information technology (IT)-medical convergence technologies, in which IT and medical technology are combined. Particularly, monitoring of the health condition of the human body is not limited to places such as hospitals, but is expanding to mobile healthcare fields that may monitor a user's health condition anytime and anywhere in daily life at home or at the office. Typical examples of bio-signals, which indicate the health condition of individuals, include an electrocardiography (ECG) signal, a photoplethysmogram (PPG) signal, an electromyography (EMG) signal, or the like, and various bio-signal sensors are being developed to measure these signals in daily life. Particularly, a PPG sensor may estimate blood pressure of a human body by analyzing the shape of pulse waves which reflect a cardiovascular state, and the like.

SUMMARY

According to an aspect of an example embodiment, an apparatus for detecting a characteristic point may include a bio-signal sensor configured to obtain a bio-signal from an object; and a processor configured to: obtain a first envelope by removing a first baseline change from an oscillometric waveform envelope of the bio-signal; obtain a second envelope by removing a second baseline change from the oscillometric waveform envelope of the bio-signal; obtain a third envelope based on the first envelope and the second envelope; and detect the characteristic point from the oscillometric waveform envelope based on the third envelope.

The bio-signal may include at least one of a photoplethysmogram (PPG) signal, an impedance plethysmogram (IPG) signal, pressure wave, and a video plethysmogram (VPG) signal.

The processor may be further configured to: generate the first envelope by applying a baseline change function in a forward direction of the oscillometric waveform envelope of the bio-signal; and generate the second envelope by applying the baseline change function in a reverse direction of the oscillometric waveform envelope of the bio-signal.

The baseline change function may be a function which outputs a minimum value for each window of the oscillometric waveform envelope of the bio-signal by sliding the oscillometric waveform envelope in units of a predetermined window size.

The window size may be set based on at least one of a user input, a user characteristic, a characteristic of an external environment, and a type of bio-information to be estimated.

The processor may be further configured to combine the first envelope and the second envelope by using at least one of a multiplication function, a weighted sum function, and a weighted multiplication function.

The processor may be configured to detect the characteristic point based on area information of the third envelope.

The processor may be further configured to: select a maximum area point of the third envelope; and detect, as the characteristic point, a maximum peak of the oscillometric waveform envelope in a predetermined time interval based on the selected maximum area point.

The maximum area point may include a time point corresponding to a maximum amplitude in a maximum area region of the third envelope.

The processor may be further configured to obtain the oscillometric waveform envelope from the obtained bio-signal.

The processor may be further configured to: perform preprocessing including at least one of equalization of the oscillometric waveform envelope, and obtaining a differential signal of the oscillometric waveform envelope.

The processor may be further configured to equalize the oscillometric waveform envelope by using at least one of a moving sum, a moving average, polynomial fitting, and Gaussian fitting.

According to an aspect of an example embodiment, an apparatus for detecting a characteristic point may include a communication interface configured to receive a bio-signal from an external device; and a processor configured to: obtain a first envelope by removing a first baseline change from an oscillometric waveform envelope of the received bio-signal; obtain a second envelope by removing a second baseline change from the oscillometric waveform envelope of the received bio-signal; obtain a third envelope based on the first envelope and the second envelope; and detect the characteristic point from the oscillometric waveform envelope based on the third envelope.

The processor may be configured to obtain the first envelope by applying a baseline change function in a forward direction of the oscillometric waveform envelope of the received bio-signal; and obtain the second envelope by applying the baseline change function in a reverse direction of the oscillometric waveform envelope of the received bio-signal.

The processor may be configured to detect a peak of the oscillometric waveform envelope of the received bio-signal as the characteristic point based on area information of the third envelope.

The communication interface may be further configured to transmit the detected characteristic point to the external device.

According to an aspect of an example embodiment, a method of detecting a characteristic point may include obtaining an oscillometric waveform envelope of a bio-signal; obtaining a first envelope by removing a first baseline change from the oscillometric waveform envelope; obtaining a second envelope by removing a second baseline change from the oscillometric waveform envelope; obtaining a third envelope based on the first envelope and the second envelope; and detecting the characteristic point from the oscillometric waveform envelope based on the third envelope.

The method may include generating the first envelope by applying a baseline change function in a forward direction of the oscillometric waveform envelope; and generating the second envelope by applying the baseline change function in a reverse direction of the oscillometric waveform envelope.

The obtaining of the third envelope may include combining the first envelope and the second envelope by using at least one of a multiplication function, a weighted sum function, and a weighted multiplication function.

The detecting of the characteristic point may include detecting the characteristic point based on area information of the third envelope.

The detecting of the characteristic point may include selecting a maximum area point of the third envelope; and detecting, as the characteristic point, a maximum peak of the oscillometric waveform envelope in a predetermined time interval based on the selected maximum area point.

The maximum area point may include a time point corresponding to a maximum amplitude in a maximum area region of the third envelope.

The method may include performing preprocessing including at least one of equalization of the oscillometric waveform envelope and obtaining a differential signal of the oscillometric waveform envelope.

According to an aspect of an example embodiment, an apparatus for estimating bio-information may include a pulse wave sensor configured to obtain a bio-signal from an object; and a processor configured to: obtain a first envelope by removing a first baseline change from an oscillometric waveform envelope of the bio-signal; obtain a second envelope by removing a second baseline change from the oscillometric waveform envelope of the bio-signal; obtain a third envelope based on the first envelope and the second envelope; detect a characteristic point from the oscillometric waveform envelope based on a third; and estimate the bio-information based on the detected characteristic point.

The processor may be configured to detect a maximum peak of the oscillometric waveform envelope as the characteristic point based on area information of the third envelope.

The apparatus may include a pressure sensor configured to measure pressure applied to the object while the bio-signal is measured from the object. The processor may be configured to estimate the bio-information based on the detected maximum peak and the measured pressure.

The bio-information may include at least one of a blood pressure, a vascular age, an arterial stiffness, an aortic pressure waveform, a vascular compliance, a stress index, and a fatigue level.

BRIEF DESCRIPTION OF THE DRAWINGS

The above and/or other aspects of the present disclosure will be more apparent from the following description of example embodiments taken in conjunction with the accompanying drawings, in which.

DETAILED DESCRIPTION

Figure 1A:
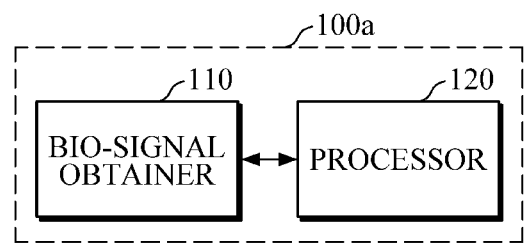
FIGS. 1A and 1B are block diagrams illustrating an apparatus for detecting a characteristic point according to an example embodiment.

Details of example embodiments are included in the following detailed description and drawings. Throughout the drawings and the detailed description, unless otherwise described, the same drawing reference numerals may refer to the same elements, features, and structures.

It should be understood that, although terms such as "first," "second," etc., may be used herein to describe various elements, these elements might not be limited by these terms. These terms may be used to distinguish one element from another. Any references to the singular form of a term may include the plural form of the term unless expressly stated otherwise. In addition, unless explicitly described to the contrary, an expression such as "comprising" or "including" should be understood to imply the inclusion of stated elements, but not the exclusion of any other elements. Also, terms such as "part," "module," etc., should be understood as a unit that is configured to perform at least one function or operation, and that may be implemented in hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for detecting a characteristic point will be described in detail with reference to the accompanying drawings. The example embodiments of the apparatus for detecting a characteristic point may be implemented in a portable device, such as a smart device, a wearable device, or the like, as well as a device in a specialized medical institution, a cuff manometer, or the like, but the apparatus for detecting a characteristic point is not limited thereto.

Figure 1B:
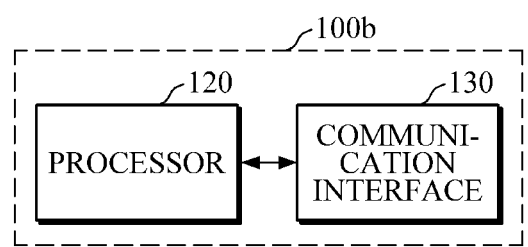

FIGS. 1A and 1B are block diagrams of an apparatus for detecting a characteristic point according to an example embodiment.

Referring to FIG. 1A, the apparatus 100a for detecting a characteristic point includes a bio-signal obtainer 110, and a processor 120.

The bio-signal obtainer 110 may be a sensor configured to measure a bio-signal from an object. The bio-signal may include a photoplethysmogram (PPG) signal, an impedance plethysmogram (IPG) signal, a pressure wave signal, a video plethysmogram (VPG), or the like. The bio-signal obtainer 110 may include various types of sensors such as an optics-based sensor, an impedance-based sensor, a pressure-based sensor, etc., depending on the types of bio-signals to be obtained, but is not limited thereto.

Hereinafter, an example embodiment will be described in detail, in which the bio-signal obtainer 110 includes an optics-based sensor (hereinafter referred to as a "pulse wave sensor") configured to measure a PPG signal (hereinafter referred to as a "pulse wave signal"), and obtain a pulse wave signal by using the pulse wave sensor and an oscillometric waveform envelope from the pulse wave signal. However, this is merely for convenience of explanation, and it will be evident to those skilled in the art that the example embodiments are not limited to the PPG signal.

The pulse wave sensor includes a light source which emits light onto an object and a detector which detects light scattered or reflected from the object. In this case, the light source may include a light emitting diode (LED) a laser diode, a phosphor, or the like. Further, the detector array include a photo diode, an image sensor, or the like, but is not limited thereto. The light source and/or the detector may be formed as an array of two or more light sources and/or detectors, and each of the light sources may emit light of different wavelengths.

The processor 120 may be configured to control various functions of the apparatus 100a for detecting a characteristic point. The processor 120 may be electrically connected to the bio-signal obtainer 110, and may control the pulse wave sensor to obtain the pulse wave signal from the object. In this case, the object may be skin tissue of the human body and may be, for example, a body part such as the back of the hand, the wrist, fingers, or the like, at which veins or capillaries are located. However, the object is not limited thereto, and may be a body part at which arteries, such as the radial artery, are located.

Based on receiving the pulse wave signal of the object, the processor 120 may remove noise from the pulse wave signal by performing, for example, band-pass filtering between 0.4 hertz (Hz) to 10 Hz, or the like. Alternatively, the processor 120 may correct the pulse wave signal by reconstructing the pulse wave signal using Fast Fourier Transform (FFT), but is not limited thereto.

The processor 120 may obtain an oscillometric waveform envelope from the pulse wave signal of the object, and detect characteristic points for estimating bio-information from the oscillometric waveform envelope. For example, the characteristic points for estimating bio-information may include a maximum peak of the oscillometric waveform envelope. In this case, bio-information may include blood pressure, vascular compliance, cardiac output, total peripheral resistance, vascular age, or the like, but is not limited thereto.

Generally, the maximum peak of the oscillometric waveform envelope may be detected, and blood pressure may be estimated by using the detected maximum peak. For example, the processor 120 may estimate systolic blood pressure and/or diastolic blood pressure by using time and/or amplitude values located at the right and left points of the maximum peak point and having a predetermined ratio (e.g., 0.5 to 0.7) to an amplitude at the detected maximum peak point, or time and/or amplitude values located at the right and left points of the maximum peak point and corresponding to points, at which a slope is maximum or minimum. In this case, the maximum peak indicates a maximum amplitude point in the oscillometric waveform envelope. However, if impulsive noise, which is caused when an object in contact with the pulse wave sensor increases or decreases pressure, is included in the pulse wave signal, or if an abnormal pulse due to arrhythmia, or the like, is included in the pulse wave signal, a maximum peak of the oscillometric waveform envelope may be inaccurately detected.

In an example embodiment of the present disclosure, in order to minimize (or reduce) inaccurate detection of the maximum peak of the oscillometric waveform envelope due to various noise included in the pulse wave signal, the maximum peak of the oscillometric waveform envelope may be detected based on area information of the oscillometric waveform envelope.

Based on a peak point being detected as a characteristic point based on the area information of the oscillometric waveform envelope, the processor 120 may be configured to provide a user with information regarding the detected characteristic point via an output component (e.g., a display, a speaker, etc.) of the apparatus 100a for detecting a characteristic point, or via an external device.

Referring to FIG. 1B, the apparatus 100b for detecting a characteristic point includes the processor 120, and a communication interface 130. The apparatus 100b for detecting a characteristic point according to an example embodiment of the present disclosure may further include the bio-signal obtainer 110 described above with reference to FIG. 1A.

The communication interface 130 may communicate with an external device under the control of the processor 120, and receive information from the external device. Additionally, the communication interface 130 may transmit information, processed by the processor 120, to the external device. Examples of the external device may include a separate sensor for measuring bio-signals from an object, a server of a medical institution for managing bio-signals, a smartphone, a tablet personal computer (PC), a laptop computer, a desktop computer, a wearable device worn by the user, or the like.

For example, the communication interface 130 may receive a bio-signal or an oscillometric waveform envelope of the bio-signal from an external device, and transmit a characteristic point, which is detected by the processor 120 by using the received bio-signal or oscillometric waveform envelope, to an external device based on a request for the characteristic point.

The communication interface 130 may communicate with an external device by using various wired or wireless communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G), fourth generation (4G), and fifth generation (5G) telecommunications, or the like. However, the foregoing communication techniques are merely examples and are not intended to be limiting.

Based on receiving the bio-signal or the oscillometric waveform envelope of the bio-signal from an external device via the communication interface 130, the processor 120 may detect a characteristic point, such as a maximum peak of the oscillometric waveform envelope, by using the bio-signal or the oscillometric waveform envelope of the bio-signal, as described above.

Based on the bio-signal obtainer 110 and the communication interface 130 being included in the apparatus 100b for detecting a characteristic point, the processor 120 may selectively control the bio-signal obtainer 110 and the communication interface 130 based on receiving a request for detecting a characteristic point from a user.

Figure 2:
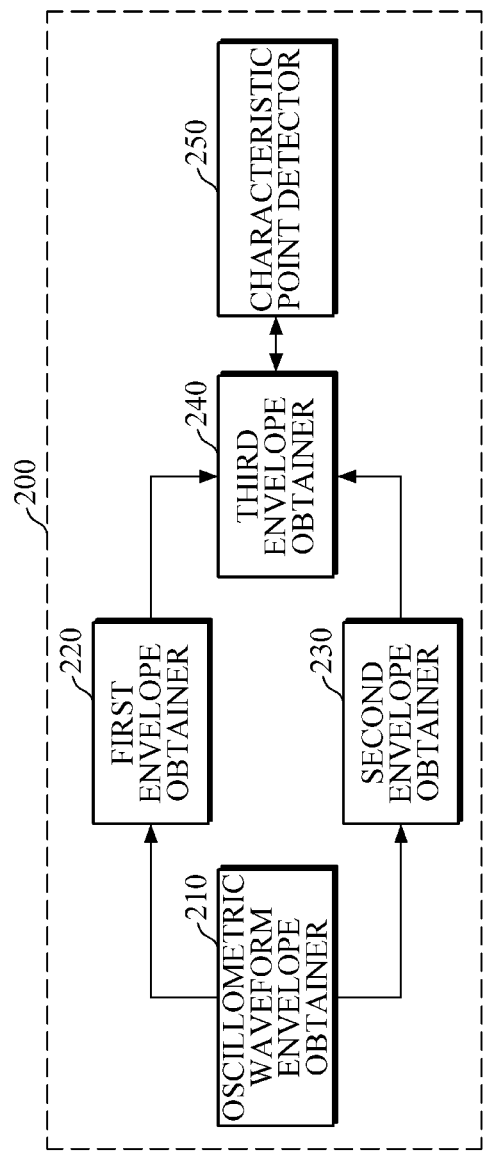
FIG. 2 is a block diagram illustrating a processor of FIGS. 1A and 1B according to an example embodiment.

FIG. 2 is a block diagram of a processor of FIGS. 1A and 1B according to an example embodiment. FIGS. 3A to 3F are diagrams of detecting a peak of an oscillometric waveform envelope according to an example embodiment.

Referring to FIG. 2, a processor 200 according to an example embodiment of the present disclosure includes an oscillometric waveform envelope obtainer 210, a first envelope obtainer 220, a second envelope obtainer 230, a third envelope obtainer 240, and a characteristic point detector 250.

Based on a bio-signal being obtained by the bio-signal obtainer 110 or via the communication interface 130, the oscillometric waveform envelope obtainer 210 may obtain an oscillometric waveform envelope from the bio-signal.

Figure 3A:
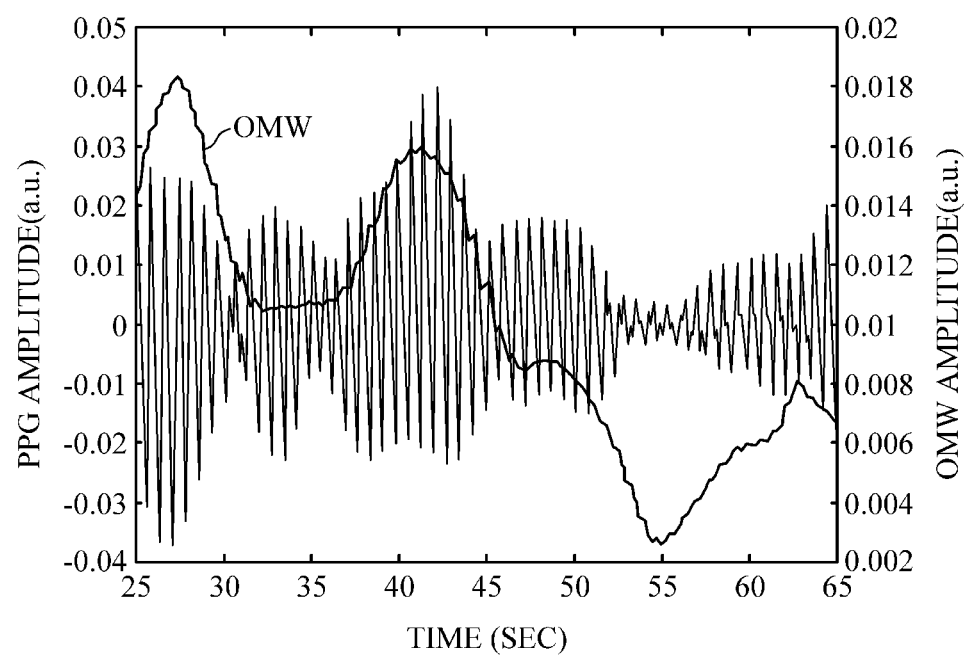
FIGS. 3A to 3F are diagrams of detecting a peak of an oscillometric waveform envelope according to an example embodiment.

FIG. 3A is a diagram illustrating a PPG signal measured by the pulse wave sensor based on a user gradually increasing contact pressure while touching the pulse wave sensor with an object according to an example embodiment. As shown in FIG. 3A, based on the user gradually increasing a pressing force applied by the object to the pulse wave sensor, the amplitude of the pulse wave signal exhibits a gradually increasing trend during a predetermined period of time.

For example, by detecting a pulse peak and a pulse onset of each pulse of the pulse wave signal, and by extracting a peak-to-peak point of the pulse wave signal waveform by subtracting an amplitude value at the pulse onset from an amplitude value at the detected pulse peak, the oscillometric waveform envelope obtainer 210 may obtain the oscillometric waveform envelope OMW. However, the oscillometric waveform envelope is not limited thereto, and may be obtained using various other methods.

Figure 3B:
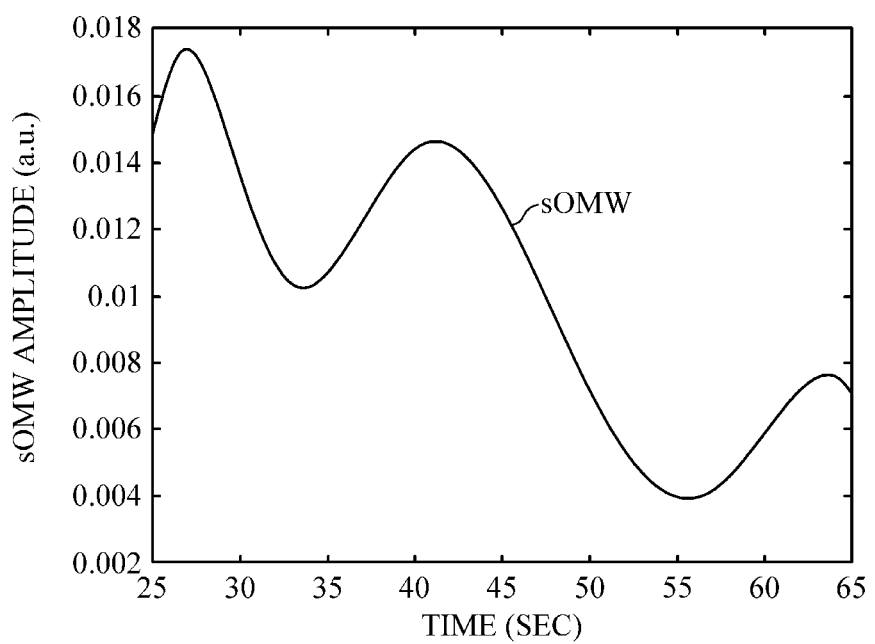

In addition, based on obtaining the oscillometric waveform envelope from the pulse wave signal, the oscillometric waveform envelope obtainer 210 may perform preprocessing on the obtained oscillometric waveform envelope. For example, the preprocessing may include equalization of the oscillometric waveform envelope. FIG. 3B is a diagram illustrating an oscillometric waveform envelope sOMW after equalization of the oscillometric waveform envelope OMW obtained in FIG. 3A according to an example embodiment. In this case, the oscillometric waveform envelope obtainer 210 may equalize the oscillometric waveform envelope by using a moving sum, a moving average, polynomial fitting, Gaussian fitting, or the like. Further, the preprocessing may include obtaining a differential signal by differentiating the obtained oscillometric waveform envelope or the equalized oscillometric waveform envelope.

The first envelope obtainer 220 may obtain a first envelope by removing a baseline change in a forward direction of the oscillometric waveform envelope of the pulse wave signal. The first envelope obtainer 220 may remove the baseline change in a forward direction by applying a baseline change function in a forward direction on a time axis of the oscillometric waveform envelope. In this case, the baseline change function may be a function which outputs a minimum value for each window by sliding the oscillometric waveform envelope in units of a predetermined window size (e.g., 30 seconds). In this case, the window size may be set to various values based on a measurement time of the pulse wave signal, a user input, user characteristics, characteristics of an external environment, types of bio-information to be estimated, or the like.

Figure 3C:
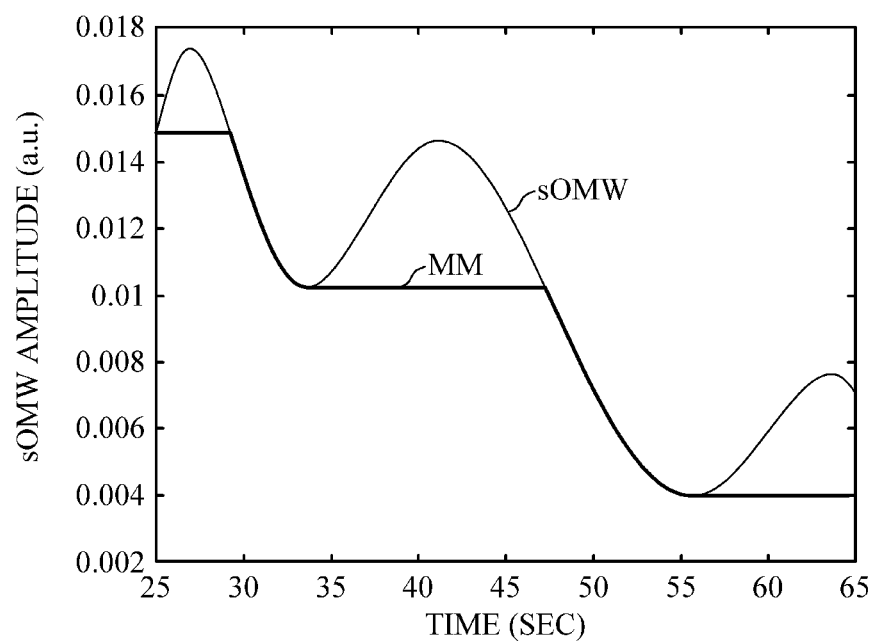

For example, referring to FIG. 3C, by sliding in a forward direction of the oscillometric waveform envelope sOMW, the baseline change function may output a baseline change MM for each window. Referring to FIG. 3E, the first envelope obtainer 220 may obtain a first envelope fOMW by removing the baseline change by subtracting the baseline change, output by the baseline change function, from the original oscillometric waveform envelope sOMW.

The second envelope obtainer 230 may obtain a second envelope by removing the baseline change in a reverse direction of the oscillometric waveform envelope of the pulse wave signal. The second envelope obtainer 230 may remove the baseline change in a reverse direction by applying the baseline change function in a reverse direction on a time axis of the oscillometric waveform envelope.

Figure 3D:
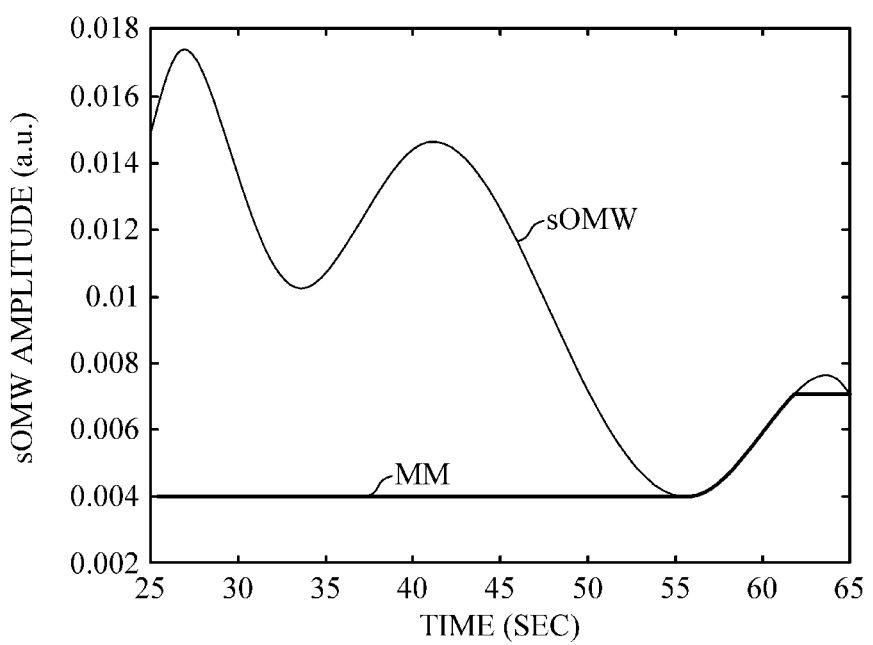
Figure 3E:
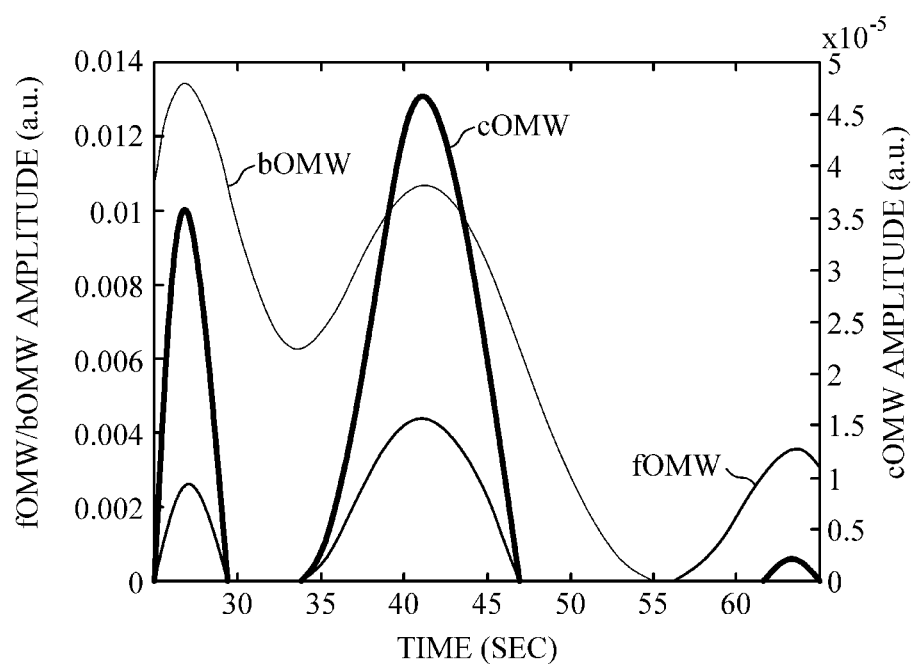

For example, referring to FIG. 3D, the baseline change function may output the baseline change MM in a reverse direction of the oscillometric waveform envelope sOMW. Referring to FIG. 3E, the second envelope obtainer 230 may obtain a second envelope bOMW by removing the baseline change in a reverse direction of the oscillometric waveform envelope by subtracting the baseline change, output by the baseline change function, from the original oscillometric waveform envelope sOMW.

The third envelope obtainer 240 may obtain a third envelope by combining the first envelope and the second envelope. For example, the third envelope obtainer 240 may combine the first envelope and the second envelope by applying a combination function including a multiplication function, a weighted sum function, a weighted multiplication function, or the like, but the combination function is not limited thereto. FIG. 3E illustrates an example of obtaining the third envelope cOMW by combining the first envelope fOMW and the second envelope bOMW.

Figure 3F:
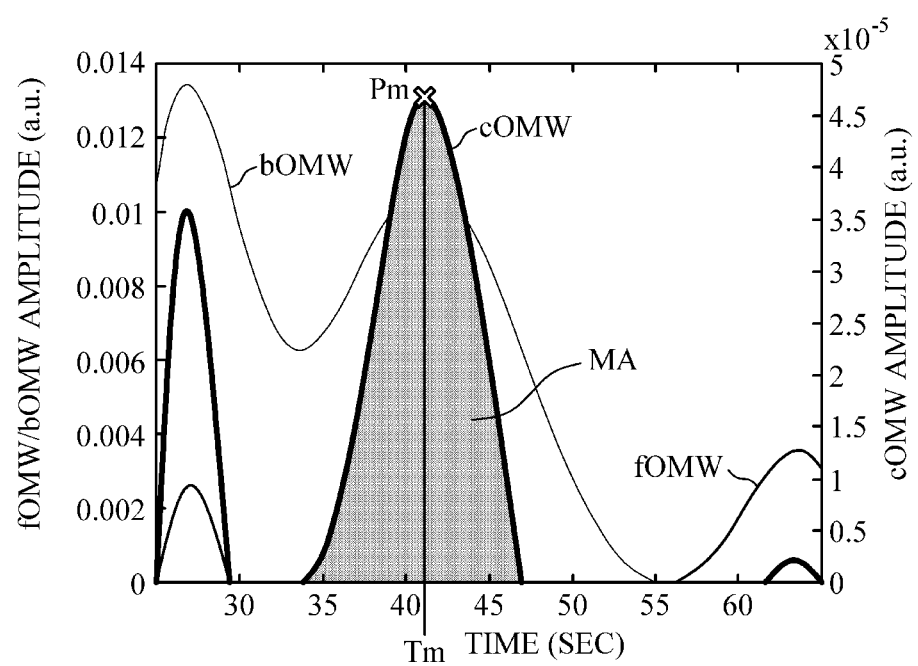

The characteristic point detector 250 may detect a peak of the oscillometric waveform envelope as a characteristic point by using the third envelope. Referring to FIG. 3F, based on obtaining the third envelope cOMW by combining the first envelope fOMW and the second envelope bOMW, the characteristic point detector 250 may detect the peak of the oscillometric waveform envelope based on area information of the third envelope cOMW.

For example, the characteristic point detector 250 may select a maximum area point Pm of the third envelope, and may detect, as the peak of the oscillometric waveform envelope, a maximum amplitude point of the original oscillometric waveform envelope sOMW in a predetermined interval based on a time Tm of the selected maximum area point. In this case, the maximum area point Pm of the third envelope may include a point corresponding to a maximum amplitude in a maximum area region MA of the third envelope cOMW. Further, the predetermined interval may be a certain interval before and after the time Tm of the maximum area point and may be, for example, five seconds before and after the time Tm of the selected maximum area point, but is not limited thereto.

Figure 4:
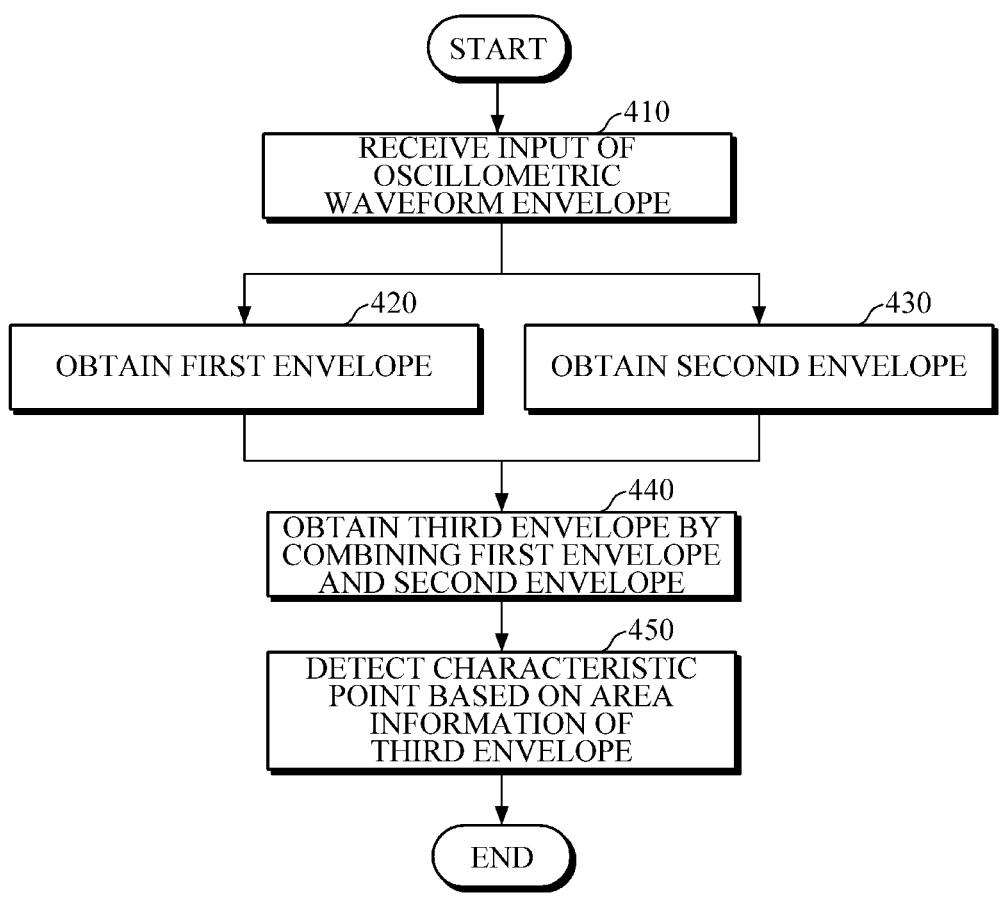
FIG. 4 is a flowchart illustrating a method of detecting a characteristic point according to an example embodiment.

FIG. 4 is a flowchart illustrating a method of detecting a characteristic point according to an example embodiment. The method of detecting a characteristic point of FIG. 4 may be performed by the apparatuses 100a and/or 100b for detecting a characteristic point according to the example embodiments of FIGS. 1A and 1B.

The apparatuses 100a and/or 100b for detecting a characteristic point may receive an input of an oscillometric waveform envelope in operation 410. For example, based on obtaining a bio-signal from an object, the apparatuses 100a and/or 100b for detecting a characteristic point may be configured to obtain an oscillometric waveform envelope from the bio-signal. Alternatively, the apparatuses 100a and/or 100b for detecting a characteristic point may receive a bio-signal or an oscillometric waveform envelope from an external device.

Based on obtaining the oscillometric waveform envelope, the apparatuses 100a and/or 100b for detecting a characteristic point may perform preprocessing, such as equalization of the oscillometric waveform envelope and/or obtaining of a differential signal of the oscillometric waveform envelope, or the like.

The apparatuses 100a and/or 100b for detecting a characteristic point may obtain a first envelope by removing a baseline change from the input oscillometric waveform envelope in operation 420. For example, the apparatuses 100a and/or 100b for detecting a characteristic point may obtain a baseline change in a forward direction by applying a pre-defined baseline change function in a forward direction on a time axis of the oscillometric waveform envelope, and obtain a first envelope by subtracting the baseline change in the forward direction from the original oscillometric waveform envelope.

Further, the apparatuses 100a and/or 100b for detecting a characteristic point may obtain a second envelope in operation 430 by removing the baseline change from the oscillometric waveform envelope received in operation 410. For example, the apparatuses 100a and/or 100b for detecting a characteristic point may obtain a baseline change in a reverse direction by applying a pre-defined baseline change function in a reverse direction on a time axis of the oscillometric waveform envelope, and obtain a second envelope by subtracting the baseline change in the reverse direction from the original oscillometric waveform envelope.

The apparatuses 100a and/or 100b for detecting a characteristic point may obtain a third envelope by combining the first envelope and the second envelope in operation 440. For example, the apparatuses 100a and 100b for detecting a characteristic point may combine the first envelope and the second envelope by applying a combination function including a multiplication function, a weighted sum function, a weighted multiplication function, or the like.

The apparatuses 100a and/or 100b for detecting a characteristic point may detect a characteristic point based on area information of the third envelope in operation 450. For example, the apparatuses 100a and 100b for detecting a characteristic point may detect a maximum area point from the third envelope, and detect a maximum peak of the oscillometric waveform envelope, obtained in operation 410, as a characteristic point in a predetermined interval based on a time of the maximum area point. In this case, the maximum area point may indicate a maximum amplitude point of the third envelope.

Figure 5A:
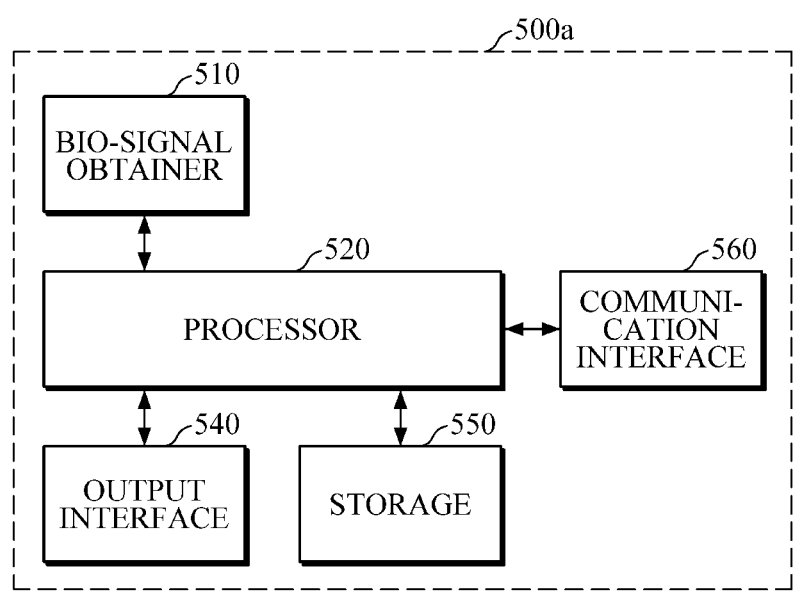
FIGS. 5A and 5B are block diagrams illustrating an apparatus for estimating bio-information according to an example embodiment.
Figure 5B:
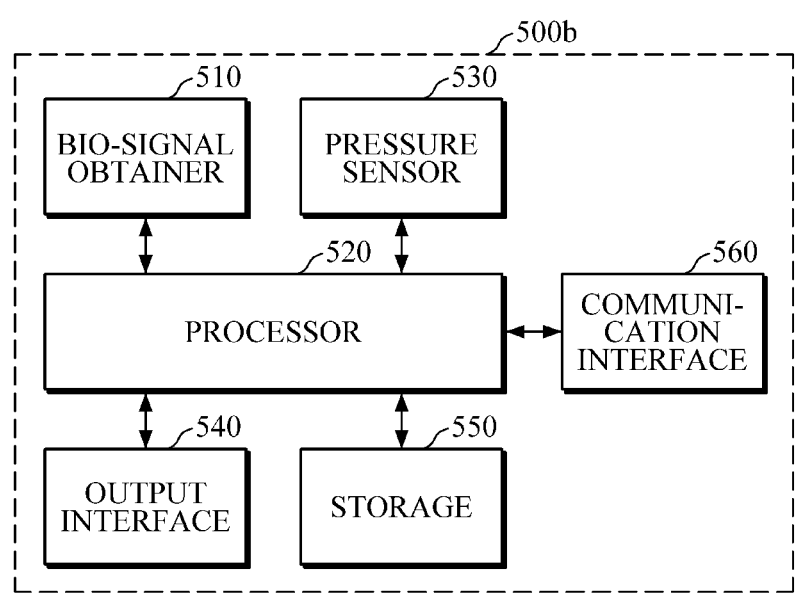

FIGS. 5A and 5B are block diagrams illustrating an apparatus for estimating bio-information according to an example embodiment.

Referring to FIGS. 5A and 5B, the apparatuses 500a and 500b for estimating bio-information include a bio-signal obtainer 510, a processor 520, an output interface 540, a storage 550, and a communication interface 560.

The bio-signal obtainer 510 may obtain a pulse wave signal from an object based on a user gradually increasing or decreasing pressure applied to the bio-signal obtainer 510. In this case, the pulse wave sensor includes a light source configured to emit light onto the object, and a detector configured to detect scattered or reflected light based on light emitted onto the object being scattered or reflected from a component of the object, and generate an electric signal based on the detected light.

The processor 520 may estimate bio-information based on the bio-signal obtained by the bio-signal obtainer 510. In this case, bio-information may include blood pressure, vascular compliance, cardiac output, total peripheral resistance, vascular age, or the like. The following description will be made using blood pressure as an example.

Based on the bio-signal being obtained, the processor 520 may obtain an oscillometric waveform envelope from the obtained bio-signal. For example, as described above, the processor 520 may detect a pulse peak and a pulse onset at each time point of the bio-signal, and obtain an oscillometric waveform envelope based on a difference between an amplitude at the pulse peak and an amplitude at the pulse onset. However, the oscillometric waveform envelope is not limited thereto.

Based on obtaining the oscillometric waveform envelope, the processor 520 may detect a characteristic point, including a peak of the oscillometric waveform envelope, by using area information of the oscillometric waveform envelope. For example, as described above, the processor 520 may obtain envelopes, from which baselines changes in a forward direction and a reverse direction are removed, by applying a baseline change function in a forward direction and a reverse direction of the oscillometric waveform envelope, respectively. Further, by combining the obtained envelopes and by using a maximum area point of one envelope obtained as a result of the combination, the processor 520 may detect a peak of the oscillometric waveform envelope, detailed description of which will be omitted.

Based on detecting the peak of the oscillometric waveform envelope, the processor 520 may estimate bio-information by using time and/or amplitude values of the peak of the oscillometric waveform envelope.

For example, the processor 520 may obtain, as additional features, a time point corresponding to an amplitude value having a predetermined ratio (e.g., 0.5 to 0.7) to an amplitude value before or after the peak point, or a time point, at which a slope is maximum/minimum, before and after the peak point. The processor 520 may estimate diastolic blood pressure based on contact pressure applied by the object to the bio-signal obtainer 510 which corresponds to a time point before the detected peak point, and estimate systolic blood pressure based on a contact pressure corresponding to a time point after the detected peak point.

For example, based on a correlation between an amplitude value at each time point of the oscillometric waveform envelope and a contact pressure, a contact pressure may be estimated from the amplitude value at each time point. In this case, a contact pressure conversion model may be pre-defined, and define a correlation between the amplitude value at each time point, or a value obtained by converting the amplitude value, and a corresponding contact pressure.

In another example, as shown in FIG. 5B, the apparatus 500b for estimating bio-information may further include a pressure sensor 530. The pressure sensor 530 may measure a change in pressure applied to an object while a bio-signal is measured from the object. For example, the pressure sensor 530 may measure a change in contact pressure applied to the pulse wave sensor while the object is in contact with the pulse wave sensor. Based on receiving the contact pressure measured by the pressure sensor 530, and obtaining time points before and after the peak point, the processor 520 may estimate systolic blood pressure and diastolic blood pressure based on contact pressure values corresponding to the time points.

Further, in addition to the peak of the oscillometric waveform envelope, the processor 520 may detect, as additional characteristic points, time and/or amplitude components related to a propagation wave and/or a reflection wave of the pulse waves, or an area in a predetermined interval of the oscillometric waveform envelope, or the like. The processor 520 may obtain features for estimating bio-information by combining the detected characteristic points, and estimate bio-information by using a pre-defined bio-information estimation model.

The output interface 540 may provide a variety of information, related to the estimated bio-information, for a user by using various output components. In this case, the output components may include a visual output components such as a display, or the like, a voice output component such as a speaker, or the like, or a haptic component, or the like, using vibration, tactile sensation, or the like, but is not limited thereto.

For example, the output interface 540 may output information, such as an estimated blood pressure value and/or a user's health condition determined based on the estimated blood pressure value, an action in response to the determined health condition, or the like. Further, the output interface 540 may output a blood pressure estimation history in the form of a graph, and provide detailed information related to estimating blood pressure at a corresponding time point selected by a user.

The storage 550 may store reference information related to estimating bio-information, the pulse wave signal, the estimated bio-information value, the detected characteristic point, or the like. In this case, the reference information may include information such as user characteristic information including a user's age, sex, health condition, or the like, a baseline change function, a bio-information estimation model, a contact pressure conversion model, or the like.

The storage 550 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static RAM (SRAM), a Read-Only Memory (ROM), an Electrically Erasable Programmable ROM (EEPROM), a Programmable ROM (PROM), a magnetic memory, a magnetic disk, and an optical disk, or the like, but is not limited thereto.

The communication interface 560 may communicate with an external device via the communication techniques described above, and transmit and receive a variety of information to and from the connected external device. In this case, examples of the external device may include a blood pressure measuring device such as a cuff manometer, a medical device related to measuring other types of bio-information, and an information processing device such as a smartphone, a tablet PC, a desktop computer, a laptop computer, or the like. For example, the communication interface 560 may receive a cuff blood pressure value, a bio-information estimation model, a contact pressure conversion model, or the like, from the external device. Further, the communication interface 560 may transmit information, such as the pulse wave signal measured by the bio-signal obtainer 510, the characteristic point detected by the processor 520, the estimated bio-information value, or the like, to the external device.

Figure 6:
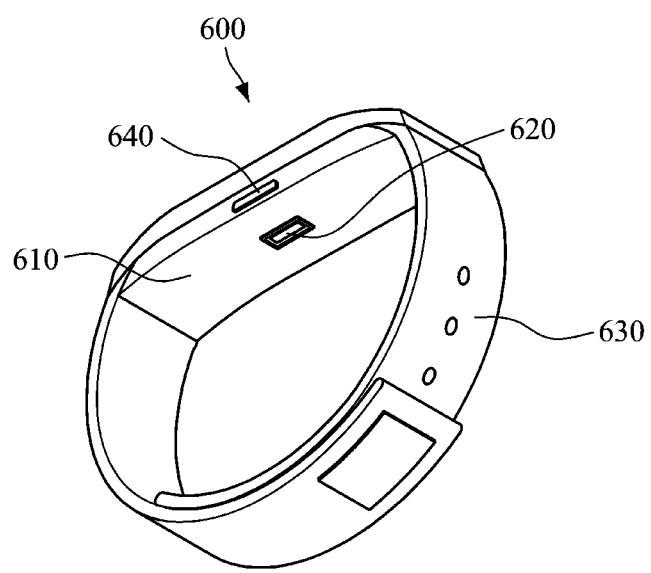
FIG. 6 is a diagram illustrating a wearable device configured to be worn on a according to an example embodiment.

FIG. 6 is a diagram illustrating a wearable device configured to be worn on a wrist according to an example embodiment. Example embodiments of the apparatuses 500a and/or 500b for estimating bio-information described above may be included in a smart watch configured to be worn on a wrist or a smart band-type wearable device, but are not limited thereto.

Referring to FIG. 6, the wearable device 600 includes a main body 610, and a strap 630.

The main body 610 may be formed to have various shapes, and may include various components which are mounted inside or outside of the main body 610 and that are configured to perform the aforementioned functions of detecting a characteristic point or estimating bio-information, as well as various other functions (e.g., a time function, an alarm function, etc.). A battery may be embedded in the main body 610 or the strap 630 to supply power to the various components of the wearable device 600.

The strap 630 may be connected to the main body 610. The strap 630 may be flexible, and configured to be wrapped around a user's wrist. The strap 630 may be bent in a manner that allows the strap 630 to be detached from the user's wrist or may be formed as a band that is not detachable. Air may be injected into the strap 630, or an airbag may be included in the strap 630, to provide the strap 630 with elasticity according to a change in pressure applied to the wrist, and the change in pressure of the wrist may be transmitted to the main body 610.

The main body 610 may include a sensor 620 for measuring a bio-signal. The sensor 620 may be mounted on one surface of the main body 610 that contacts the user's wrist based on the main body 610 being worn on a user's wrist. For example, the sensor 620 may include a light source configured to emit light onto the wrist, and a detector configured to detect light scattered or reflected from body tissue such as a skin surface, blood vessels, or the like. However, the sensor 620 is not limited thereto, and may include an impedance-based sensor, a pressure-based sensor, or the like.

In addition, a processor may be mounted in the main body 610, and may be electrically connected to various components of the wearable device 600 to control operations thereof.

The processor may control the sensor 620 based on an occurrence of a bio-information estimation event. The bio-information estimation event may be generated based on a user's command input via a touch screen, a button 640, a display, or the like, at predetermined bio-information estimation intervals, by monitoring a bio-information estimation result, or the like.

Based on the sensor 620 measuring the bio-signal, the processor may obtain an oscillometric waveform envelope, and remove baseline changes in a forward direction and a reverse direction of the oscillometric waveform envelope. Further, the processor may combine envelopes, from each of which the baseline changes are removed in the forward direction and the reverse direction, and detect a peak of the oscillometric waveform envelope based on area information of the combined oscillometric waveform envelope generated as a result of the combination. By using the peak of the oscillometric waveform envelope, the processor may estimate bio-information related to cardiovascular conditions, such as blood pressure.

The display may be mounted on a front surface of the main body 610, and may be a touch panel having a touch screen configured to sense a touch input. The display may receive a touch input from a user, transmit the received touch input to the processor, and display a processing result of the processor. For example, the display may display a bio-information estimation result, and display additional information such as a bio-information estimation history, a change in health condition, warning information, or the like, along with the estimation result.

A storage, that is configured to store the processing result of the processor and a variety of information, may be mounted in the main body 610. In this case, the variety of information may include information related to estimating bio-information, as well as information related to other functions of the wearable device 600.

In addition, the main body 610 may include a button 640 that is configured to receive a user's command, and transmit the received command to the processor. The button 640 may include a power button to input a command to turn on/off the wearable device 600.

A communication interface, that is configured to communicate with an external device, may be mounted in the main body 610. The communication interface may transmit a bio-information estimation result to an external device to permit the external device (e.g., a mobile terminal) to output the estimation result or store the estimation result in a storage module of the external device. Further, the communication interface may receive information for supporting various other functions of the wearable device 600, or the like, from the external device.

Figure 7:
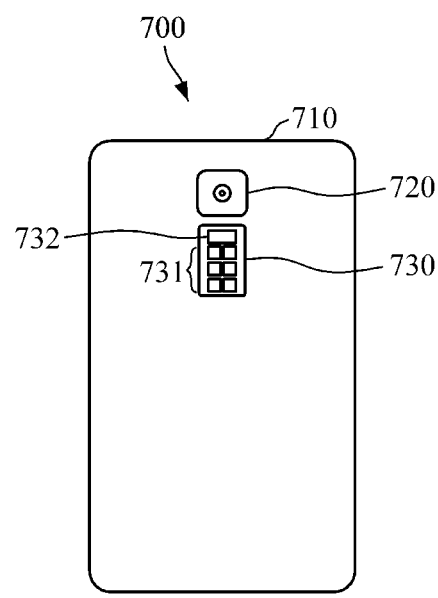
FIG. 7 is a diagram illustrating a smart device according to an example embodiment.

FIG. 7 is a diagram illustrating a smart device, to which embodiments of the apparatuses 500*a* and/or 500*b* for estimating bio-information described above are applied according to an example embodiment. In this case, the smart device may be a smartphone, a tablet PC, or the like, but s not limited thereto.

Referring to FIG. 7, the smart device 700 may include a main body 710 and a sensor 730 mounted on one surface of the main body 710. The sensor 730 may include one or more light sources 731, and a detector 732. However, the sensor 730 is not limited thereto, and may include an impedance-based sensor, a pressure-based sensor, or the like. As shown in FIG. 7, the sensor 730 may be mounted on a rear surface of the main body 710, but is not limited thereto, and may be configured in combination with a fingerprint sensor or a touch panel mounted on a front surface of the main body 710.

A display may be mounted on a front surface of the main body 710. The display may visually display a bio-information estimation result, or the like. The display may include a touch panel, and may receive information input via the touch panel, and transmit the received information to the processor.

An image sensor 720 may be mounted in the main body 710. Based on a user's finger approaching the sensor 730 to measure a bio-signal, the image sensor 720 may capture an image of the finger, and transmit the captured image to the processor. In this case, based on the image of the finger, the processor may identify a relative position of the finger with respect to an actual position of the sensor 730, and provide the relative position of the finger for the user via the display, so as to guide the user to accurately contact the sensor 730 with the finger.

The processor may detect a peak of an oscillometric waveform envelope by using a bio-signal measured by the sensor 730. As described above in detail, the processor may remove baseline changes in a forward direction and a reverse direction of the oscillometric waveform envelope, combine envelopes, from each of which the baseline changes are removed in the forward direction and the reverse direction, and detect a peak of the oscillometric waveform envelope based on area information of the combined oscillometric waveform envelope. By using the peak of the oscillometric waveform envelope, the processor may estimate bio-information, and output the estimation result via the display.

The example embodiments of the present disclosure may be implemented by computer-readable code written on a non-transitory computer-readable medium and executed by a processor. The non-transitory computer-readable medium may be any type of recording device in which data is stored in a computer-readable manner.

Examples of the non-transitory computer-readable recording medium include a ROM, a RAM, a CD-ROM, a magnetic tape, a floppy disc, an optical data storage, and a carrier wave (e.g., data transmission via the Internet). The computer-readable medium may be distributed over a plurality of computer systems connected to a network so that computer-readable code is written thereto and executed therefrom in a decentralized manner. Functional programs, code, and code segments for implementing the example embodiments may be deduced by one of ordinary skill in the art.

has Although example embodiments have been described herein, it will be understood by those skilled in the art that various changes and modifications may be made without changing technical ideas and features of the present disclosure. Thus, it is clear that the above-described example embodiments are illustrative in all aspects and are not intended to limit the present disclosure.

What is claimed is:

1. An apparatus for detecting a characteristic point of bio-information, the apparatus comprising:
   a pulse wave sensor configured to obtain a bio-signal from a test subject;
   a processor configured to obtain the characteristic point from the bio-signal by:
   obtaining a first envelope by removing a first baseline change from an oscillometric waveform envelope of the bio-signal;
   obtaining a second envelope by removing a second baseline change from the oscillometric waveform envelope of the bio-signal;
   obtaining a third envelope based on the first envelope and the second envelope; and
   detecting the characteristic point from the oscillometric waveform envelope based on the third envelope, the characteristic point being used to estimate bio-information including at least one of: a blood pressure, a vascular age, an arterial stiffness, an aortic pressure waveform, a vascular compliance, a stress index, and a fatigue level of the test subject;
   an image sensor configured to capture an image of a body part of the test subject relative to the pulse wave sensor; and
   a display for displaying guidance information for placement of the body part of the test subject in relation to the pulse wave sensor, based on the captured image.

2. The apparatus of claim 1, wherein the bio-signal comprises a photoplethysmogram (PPG) signal.

3. The apparatus of claim 1, wherein the processor is further configured to:
   generate the first envelope by applying a baseline change function in a forward direction of the oscillometric waveform envelope of the bio-signal; and
   generate the second envelope by applying the baseline change function in a reverse direction of the oscillometric waveform envelope of the bio-signal.

4. The apparatus of claim 3, wherein the baseline change function is a function which outputs a minimum value for each window of the oscillometric waveform envelope of the bio-signal by sliding the oscillometric waveform envelope in units of a predetermined window size.

5. The apparatus of claim 4, wherein the predetermined window size is set based on at least one of a user input, a user characteristic, a characteristic of an external environment, and a type of bio-information to be estimated.

6. The apparatus of claim 1, wherein the processor is further configured to combine the first envelope and the second envelope by using at least one of a multiplication function, a weighted sum function, and a weighted multiplication function.

7. The apparatus of claim 1, wherein the processor is configured to detect the characteristic point based on area information of the third envelope.

8. The apparatus of claim 7, wherein the processor is further configured to:
select a maximum area point of the third envelope; and
detect, as the characteristic point, a maximum peak of the oscillometric waveform envelope in a predetermined time interval based on the selected maximum area point.

9. The apparatus of claim 8, wherein the maximum area point comprises a time point corresponding to a maximum amplitude in a maximum area region of the third envelope.

10. The apparatus of claim 1, wherein the processor is further configured to obtain the oscillometric waveform envelope from the obtained bio-signal.

11. The apparatus of claim 10, wherein the processor is further configured to perform preprocessing including at least one of equalization of the oscillometric waveform envelope, and obtaining a differential signal of the oscillometric waveform envelope.

12. The apparatus of claim 11, wherein the processor is further configured to equalize the oscillometric waveform envelope by using at least one of a moving sum, a moving average, polynomial fitting, and Gaussian fitting.

13. An apparatus for detecting a characteristic point, the apparatus comprising:
a receiver configured to receive a pulse wave signal representative of bio information of a test subject from an external device;
a processor configured to obtain the characteristic point from the pulse wave signal by:
obtaining a first envelope by removing a first baseline change from an oscillometric waveform envelope of the pulse wave signal;
obtaining a second envelope by removing a second baseline change from the oscillometric waveform envelope of the pulse wave signal;
obtaining a third envelope based on the first envelope and the second envelope; and
detecting the characteristic point from the oscillometric waveform envelope based on the third envelope, wherein the characteristic point is used to estimate bio-information including at least one of: a blood pressure, a vascular age, an arterial stiffness, a vascular compliance, a stress index, and a fatigue level of the test subject;
an image sensor configured to capture an image of a body part of the test subject relative to a pulse wave sensor; and
a display for displaying guidance information for placement of the body part of the test subject in relation to the pulse wave sensor, based on the captured image.

14. The apparatus of claim 13, wherein the processor is configured to:
obtain the first envelope by applying a baseline change function in a forward direction of the oscillometric waveform envelope of the pulse wave signal; and
obtain the second envelope by applying the baseline change function in a reverse direction of the oscillometric waveform envelope of the pulse wave signal.

15. The apparatus of claim 13, wherein the processor is configured to detect a peak of the oscillometric waveform envelope of the pulse wave signal as the characteristic point based on area information of the third envelope.

16. The apparatus of claim 13, further comprising a transmitter to transmit the detected characteristic point to the external device.

17. A method of detecting a characteristic point in a pulse wave signal representative of bio-information in a test subject, the method comprising:
obtaining an oscillometric waveform envelope of the pulse wave signal using a pulse wave sensor;
using one or more processors to obtain the characteristic point from the pulse wave signal by:
obtaining a first envelope by removing a first baseline change from the oscillometric waveform envelope;
obtaining a second envelope by removing a second baseline change from the oscillometric waveform envelope;
obtaining a third envelope based on the first envelope and the second envelope; and
detecting the characteristic point from the oscillometric waveform envelope based on the third envelope, wherein the characteristic point is used to estimate bio-information including at least one of: a blood pressure, a vascular age, an arterial stiffness, a vascular compliance, a stress index, and a fatigue level of the test subject;
capturing an image of a body part of the test subject relative to the pulse wave sensor; and
displaying guidance information for placement of the body part of the test subject in relation to the pulse wave sensor, based on the captured image.

18. The method of claim 17, further comprising:
generating the first envelope by applying a baseline change function in a forward direction of the oscillometric waveform envelope; and
generating the second envelope by applying the baseline change function in a reverse direction of the oscillometric waveform envelope.

19. The method of claim 17, wherein the obtaining of the third envelope comprises combining the first envelope and the second envelope by using at least one of a multiplication function, a weighted sum function, and a weighted multiplication function.

20. The method of claim 17, wherein the detecting of the characteristic point comprises detecting the characteristic point based on area information of the third envelope.

21. The method of claim 20, wherein the detecting of the characteristic point comprises:
selecting a maximum area point of the third envelope; and
detecting, as the characteristic point, a maximum peak of the oscillometric waveform envelope in a predetermined time interval based on the selected maximum area point.

22. The method of claim 21, wherein the maximum area point comprises a time point corresponding to a maximum amplitude in a maximum area region of the third envelope.

23. The method of claim 17, further comprising performing preprocessing including at least one of equalization of the oscillometric waveform envelope and obtaining a differential signal of the oscillometric waveform envelope.

24. An apparatus for estimating bio-information, the apparatus comprising:
a pulse wave sensor configured to obtain a bio-signal from a test subject;
a processor configured to estimate the bio-information from the bio-signal by:

obtaining a first envelope by removing a first baseline change from an oscillometric waveform envelope of the bio-signal;

obtaining a second envelope by removing a second baseline change from the oscillometric waveform envelope of the bio-signal;

obtaining a third envelope based on the first envelope and the second envelope;

detecting a characteristic point from the oscillometric waveform envelope based on the third envelope; and estimating the bio-information based on the detected characteristic point, wherein the characteristic point is used to estimate at least one of: a blood pressure, a vascular age, an arterial stiffness, a vascular compliance, a stress index, and a fatigue level of the test subject;

an image sensor configured to capture an image of a body part of the test subject relative to the pulse wave sensor; and a display for displaying guidance information for placement of the body part of the test subject in relation to the pulse wave sensor, based on the captured image.

25. The apparatus of claim 24, wherein the processor is configured to detect a maximum peak of the oscillometric waveform envelope as the characteristic point based on area information of the third envelope.

26. The apparatus of claim 25, further comprising:

a pressure sensor configured to measure pressure applied to the test subject while the bio-signal is measured from the test subject, wherein the processor is configured to estimate the bio-information based on the detected maximum peak and the measured pressure.

27. A method comprising:

obtaining an oscillometric waveform envelope of a bio-signal of a test subject using a pulse wave sensor;

using one or more processors to estimate bio information from the bio-signal by:

obtaining a first envelope by removing a set of first baseline changes of a set of windows of the oscillometric waveform envelope in a forward direction of a time axis of the oscillometric waveform envelope of the bio-signal;

obtaining a second envelope by removing a set of second baseline changes of the set of windows of the oscillometric waveform envelope in a reverse direction of the time axis of the oscillometric waveform envelope of the bio-signal;

obtaining a third envelope based on the first envelope and the second envelope;

detecting a characteristic point of the oscillometric waveform envelope based on the third envelope; and estimating bio-information of the test subject based on the characteristic point, wherein the characteristic point represents at least one of: a blood pressure, a vascular age, an arterial stiffness, a vascular compliance, a stress index, and a fatigue level of the test subject;

capturing an image of a body part of the test subject relative to the pulse wave sensor; and displaying guidance information for placement of the body part of the test subject in relation to the pulse wave sensor, based on the captured image.

* * * * *